(12) United States Patent
Orbay

(10) Patent No.: US 6,866,665 B2
(45) Date of Patent: Mar. 15, 2005

(54) BONE FRACTURE FIXATION SYSTEM WITH SUBCHONDRAL AND ARTICULAR SURFACE SUPPORT

(75) Inventor: Jorge L. Orbay, Miami, FL (US)

(73) Assignee: Hand Innovations, LLC, DE (US)

( * ) Notice: Subject to any disclaimer, the term of this patent is extended or adjusted under 35 U.S.C. 154(b) by 6 days.

(21) Appl. No.: 10/401,089

(22) Filed: Mar. 27, 2003

(65) Prior Publication Data

US 2004/0193163 A1 Sep. 30, 2004

(51) Int. Cl.[7] .............................................. A61B 17/56
(52) U.S. Cl. ...................................................... 606/69
(58) Field of Search ............................. 606/53, 60, 69, 606/86

(56) References Cited

U.S. PATENT DOCUMENTS

| | | | |
|---|---|---|---|
| 3,741,205 A | 6/1973 | Markolf et al. | 128/92 B |
| 4,794,919 A | 1/1989 | Nilsson | 128/92 |
| 4,867,144 A | 9/1989 | Karas et al. | 128/92 |
| 5,006,120 A | 4/1991 | Carter | 606/69 |
| 5,015,248 A * | 5/1991 | Burstein et al. | 606/74 |
| 5,151,103 A | 9/1992 | Tepic et al. | 606/69 |
| 5,197,966 A * | 3/1993 | Sommerkamp | 606/69 |
| 5,527,311 A * | 6/1996 | Procter et al. | 606/61 |
| 5,586,985 A | 12/1996 | Putnam et al. | 606/69 |
| 5,601,553 A * | 2/1997 | Trebing et al. | 606/61 |
| 5,676,667 A | 10/1997 | Hausman | 606/69 |
| 5,709,686 A | 1/1998 | Talos et al. | 606/69 |
| 5,718,705 A | 2/1998 | Sammarco | 606/69 |
| 5,749,872 A * | 5/1998 | Kyle et al. | 606/69 |
| 5,853,413 A | 12/1998 | Carter et al. | 606/69 |
| 6,096,040 A * | 8/2000 | Esser | 606/69 |
| 6,221,073 B1 * | 4/2001 | Weiss et al. | 606/60 |
| D443,060 S * | 5/2001 | Benirschke et al. | D24/155 |
| 6,270,499 B1 | 8/2001 | Leu et al. | 606/64 |
| 6,355,041 B1 | 3/2002 | Martin | 606/62 |
| 6,358,250 B1 * | 3/2002 | Orbay | 606/69 |
| 6,364,882 B1 * | 4/2002 | Orbay | 606/69 |
| 6,440,135 B2 | 8/2002 | Orbay et al. | 606/69 |
| 6,468,278 B1 | 10/2002 | Mückter | 606/69 |
| 6,527,775 B1 | 3/2003 | Warburton | 606/62 |
| 2003/0105461 A1 | 6/2003 | Putnam | 606/69 |

OTHER PUBLICATIONS

"Summary of Safety and Effectiveness Information"; Synthes®; Jul. 29, 1998.
"The Distal Radius Plate Instrument and Implant Set", Technique Guide, SYNTHES®, Paoli, PA 1995.
"The Titanium Distal Radius Plate", Technique Guide, SYNTHES®, Paoli, PA, 1995.
"SCS™/D Distal Radius Plate System: Dorsal", Avanta, 1997.
"SCS™/V Distal Radius Plate: Volar", Avanta, 1998.
"Advances in distal Radius Fracture Management(D)", transcript of American Academy of Orthopaedic Surgeons 2001 Conference, pp. 134–151, Feb. 28, 2001, including article by Matthew D. Putnam, MD, entitled "Repair and Rehabilitation of Distal Radius Fractures:: The Role of Subchondral Fixation" at pp. 144–147.

* cited by examiner

Primary Examiner—Eduardo C. Robert
Assistant Examiner—Anu Ramana
(74) Attorney, Agent, or Firm—Gordon & Jacobson, P.C.

(57) ABSTRACT

A volar plate includes a head portion with two sets of pegs. The first set of the pegs is substantially linearly arranged and the axes of the pegs are preferably oblique relative to each other, and are preferably angled relative to each other in two dimensions. The second set of pegs is provided relatively distal of the first set through a buttress of the head portion of the plate. The second set of pegs is preferably angled relative to the plate such that the pegs are oriented substantially perpendicular to the body of the plate and extend between the pegs of the first set. The first set of pegs provides support for subchondral bone fragments, while the second set of pegs provides support behind the articular bone surface.

58 Claims, 1 Drawing Sheet

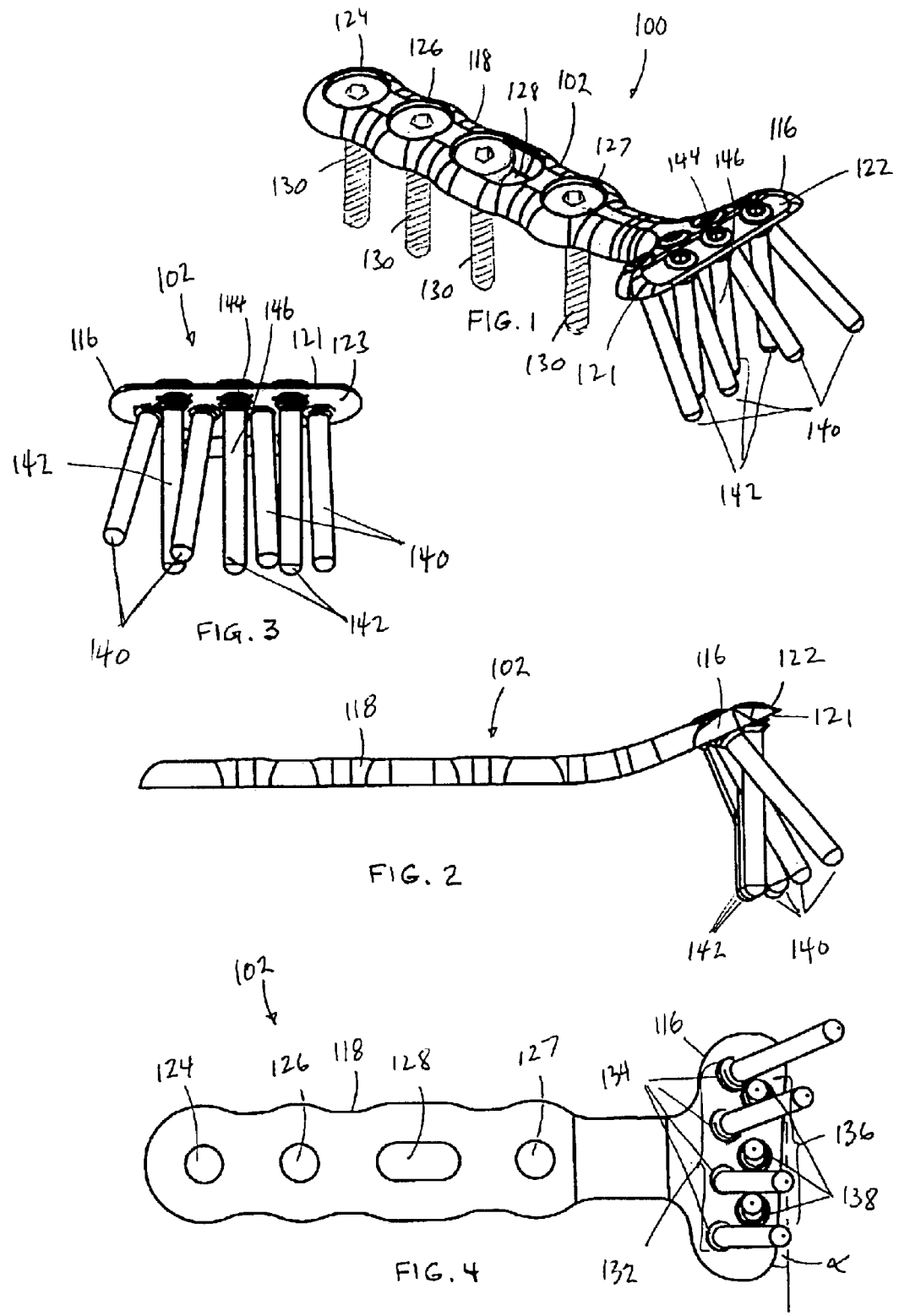

US 6,866,665 B2

BONE FRACTURE FIXATION SYSTEM WITH SUBCHONDRAL AND ARTICULAR SURFACE SUPPORT

BACKGROUND OF THE INVENTION

1. Field of the Invention

This invention relates broadly to surgical implants. More particularly, this invention relates to a bone fracture fixation system having support pegs.

2. State of the Art

Fracture to the metaphyseal portion of a long bone can be difficult to treat. Improper treatment can result in deformity and long-term discomfort.

By way of example, a Colles' fracture is a fracture resulting from compressive forces being placed on the distal radius, and which causes backward displacement of the distal fragment and radial deviation of the hand at the wrist. Often, a Colles' fracture will result in multiple bone fragments which are movable and out of alignment relative to each other. If not properly treated, such fractures result in permanent wrist deformity. It is therefore important to align the fracture and fixate the bones relative to each other so that proper healing may occur.

Alignment and fixation of a metaphyseal fracture are typically performed by one of several methods: casting, external fixation, interosseous wiring, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Interosseous wiring is an invasive procedure whereby screws are positioned into the various fragments and the screws are then wired together as bracing. This is a difficult and time-consuming procedure. Moreover, unless the bracing is quite complex, the fracture may not be properly stabilized. Plating utilizes a stabilizing metal plate typically against the dorsal side of the bones, and a set of parallel pins extending from the plate into holes drilled in the bone fragments to provide stabilized fixation of the fragments. However, the currently available plate systems fail to provide desirable alignment and stabilization. In particular, with a distal radius fracture, there is a need for alignment and stabilization of both the subchondral bone and the articular surfaces which is not met by current plates.

SUMMARY OF THE INVENTION

It is therefore an object of the invention to provide an improved volar fixation system for distal radius fractures.

It is another object of the invention to provide a volar fixation system that desirably aligns and stabilizes multiple bone fragments in a fracture to permit proper healing.

It is an additional object of the invention to provide a volar plate system which provides support for articular and subchondral surfaces.

In accord with these objects, which will be discussed in detail below, a volar fixation system is provided which generally includes a T-shaped plate intended to be positioned against the volar side of the radial bone, a plurality of bone screws for securing the plate along a non-fractured portion of the radial bone, and a plurality of bone pegs sized to extend from the plate and into bone fragments at the metaphysis of a radius bone.

The plate is generally T-shaped, defining an elongate body, a head portion angled up relative to the body, a first side which is intended to contact the bone, and a second side opposite the first side. The body portion includes a plurality of countersunk screw holes for the extension of the bone screws therethrough. The head portion includes a plurality of threaded peg holes for receiving the pegs therethrough. According to the invention, the peg holes are arranged into first and second sets. The first set of the peg holes is substantially linearly arranged and also preferably arranged such that the holes are positioned increasingly distal in a medial to lateral direction along the second side. Axes through the first set of holes are preferably oblique relative to each other, and are preferably angled relative to each other in two dimensions such that pegs inserted therethrough are similarly obliquely angled relative to each other. The second set of peg holes is provided relatively distal of the first set. The holes of the second set are also substantially linearly arranged, and the holes define axes that are preferably substantially parallel. More preferably, the second set of peg holes are angled relative to the plate such that pegs positioned within the holes are oriented substantially perpendicular to the body of the plate and extend between the pegs of the first set. Pegs in the first set of peg holes provide support for the dorsal aspect of the subchondral bone fragments, while pegs in the second set of peg holes provide support for the volar aspect of the subchondral bone, behind the articular bone surface.

Additional objects and advantages of the invention will become apparent to those skilled in the art upon reference to the detailed description taken in conjunction with the provided figures.

BRIEF DESCRIPTION OF THE DRAWINGS

FIG. 1 is a perspective view of a volar fixation system according to the invention;

FIG. 2 is a side elevation view of a volar plate and pegs of the volar fixation system of the invention;

FIG. 3 is a distal end view of a volar plate and pegs of the volar fixation system of the invention; and FIG. 4 is a bottom view of a volar plate and pegs of the volar fixation system of the invention.

DETAILED DESCRIPTION OF THE PREFERRED EMBODIMENTS

Turning now to FIGS. 1 through 4, a fracture fixation system 100 according to the invention is shown. The system 100 is particularly adapted for aligning and stabilizing multiple bone fragments in a Colles' fracture.

According the first embodiment, the system 100 generally includes a substantially rigid T-shaped plate 102, commonly called a volar plate, bone screws 130, and pegs 140, 142. The plate 102 is intended to be positioned against the volar side of a fractured radius bone. The T-shaped plate 102 defines a head portion 116, and an elongate body portion 118 preferably angled relative to the head portion. The angle between the head portion 116 and the body portion 118 is preferably approximately 23° and bent at a radius of preferably approximately 0.7 to 0.8 inch. A distal buttress 121 of the head portion 116 (i.e., the portion of the head portion distal a first set of peg holes 134, discussed below) is preferably angled proximally toward the medial side at an angle α, e.g. 5°, relative to a line that is perpendicular to the body portion 118 (FIG. 4). In addition, an upper surface 122 of the buttress 121 is preferably angled relative to the remainder of the head portion 116 such that that upper surface 122 is substantially parallel to the body portion 118 and the buttress tapers in thickness distally (FIG. 2). The lower surface 123 of the head portion 116 is preferably planar. The plate 102 has a thickness of preferably approximately 0.1 inch, and is preferably made from a titanium alloy, such as Ti-6Al-4V.

The body portion 118 includes four preferably countersunk screw holes 124, 126, 127, 128 for the extension of bone screws 130 therethrough (FIG. 2). One of the screw holes, 128, is preferably generally oval in shape permitting longitudinal movement relative to the shaft of a bone screw.

The head portion 116 includes a first set 132 of threaded peg holes 134 (for placement of pegs 140 therein) and a second set 136 of threaded peg holes 138 (for placement of pegs 142 therein). The peg holes 134 of the first set are arranged along a line or slight curve. The first set of peg holes 134 are also preferably arranged such that the holes are positioned in an increasingly distal manner in the medial to lateral direction. The peg holes 134 of the first set are preferably located approximately 0.25 inch apart. Axes through the first set of peg holes (indicated by the pegs 140 extending therethrough) are preferably oblique relative to each other, and are preferably angled relative to each other in two dimensions.

The second set 136 of peg holes 138 is provided relatively distal of the first set 132 and is most preferably located in the buttress 121. The peg holes 138 of the second set are preferably substantially linearly arranged and are preferably substantially parallel to the arrangement of peg holes 134. Each of the peg holes 138 preferably defines an axis perpendicular to the upper surface 122 of the buttress 121 and also substantially perpendicular to the body portion 116 of the plate 102. Pegs 142, placed within the peg holes 138, are preferably angled relative to pegs 140 inserted through peg holes 134, and may extend between pegs 140 in an interleaved manner. In addition, pegs 142 (and axes through peg holes 134) preferably project distally peg holes 138 and pegs 140 (and axes through pegs holes 138). Alternatively, pegs 140 through peg holes 134 and pegs 142 through peg holes 138 may be oriented substantially parallel or in other relative configurations.

The pegs 140 and 142 include a threaded head, e.g., 144, and a shaft, e.g., 146, which is preferably non-threaded. Exemplar pegs are described in more detail in U.S. Pat. No. 6,364,882, which is hereby incorporated by reference herein in its entirety.

In use, a relatively small incision is made over the fracture, and the pronator quadratus is reflected from its radial insertion exposing the entire distal radius ulnarly to the distal radioulnar joint. The plate 102 is brought against the bone and aligned with the fracture such that the first set 132 of peg holes 134 is situated substantially over the bone fragment or fragments. A first screw hole is drilled by the surgeon through hole 128 and into the radius bone. A first bone screw 130 is then inserted through the hole 128 in the plate 102 and secured to the bone. Prior to fully tightening the bone screw 130 against the plate, the plate may be longitudinally adjusted relative to the screw. Once the proper position is established, the first screw can be tightened, and additional screws 130 may be inserted through the other screw holes 124, 126, 127 in a like manner.

The fractured bones are adjusted under the plate 102 into their desired positions for healing. The surgeon then drills through peg holes 134, 138 into the bone for the pegs 140, 142. Pegs 140 are then inserted through the peg holes 134 and into the holes drilled into the fragments, and the heads of the pegs are threadably engaged in the volar plate. Similarly, pegs 142 are inserted through peg holes 138 and holes drilled behind the articular surface, and fixed to the plate, to provide support thereat. The first set of pegs 140 defines projections which support central and/or dorsal aspects of the subchondral bone, which is particularly desired in dorsally unstable fractures of the distal radius. The second set of pegs 142 defines projections which provide support at the volar aspect behind the articular surface of the bone surface. The sets 132, 136 of pegs preferably laterally overlap to provide tangential cradling of the subchondral bone. Preferably, at least three pegs are provided in each set 132, 136 to provide a preferred degree of subchondral support. The fracture fixation system thereby defines a framework which substantially tangentially supports the bone fragments in their proper orientation. In accord with an alternate less preferred embodiment, suitable support may also be provided where the pegs 140 and 142 are parallel to each other or in another relative orientation.

While fixed single-angle pegs have been disclosed for use with the plate (i.e., the pegs may be fixed in respective threaded peg holes only coaxial with an axis defined by the respective peg holes), it is appreciated that an articulating peg system, such as that disclosed in U.S. Pat. No. 6,440,135 or co-owned and co-pending U.S. Ser. No. 10/159,612, both of which are hereby incorporated by reference herein in their entireties, may also be used. In such articulating peg systems, the peg holes and pegs are structurally adapted such that individual pegs may be fixed at any angle within a range of angles may also be used for either or both sets 132, 136 of peg holes and associated pegs. In addition, while less preferable, one or both sets of the pegs may be replaced by preferably blunt tines which are integrated into the plate such that the plate and tines are unitary in construct. Similarly, other elongate projections may be coupled to the plate define the desired support.

There have been described and illustrated herein an embodiment of a volar fixation system and a method of aligning and stabilizing a Colles' fracture. While a particular embodiment of the invention have been described, it is not intended that the invention be limited thereto, as it is intended that the invention be as broad in scope as the art will allow and that the specification be read likewise. Thus, while particular materials for the elements of the system have been disclosed, it will be appreciated that other materials may be used as well. In addition, while a particular number of screw holes in the volar plate and bone screws have been described, it will be understood another number of screw holes and screws may be provided. Further, fewer screws than the number of screw holes may be used to secure to the volar plate to the radius bone. Also, fewer or more peg holes and bone pegs may be used, preferably such that at least two pegs angled in two dimensions relative to each other are provided. In addition, while a particular preferred angle between the head portion and body portion has been disclosed, other angles can also be used. It will therefore be appreciated by those skilled in the art that yet other modifications could be made to the provided invention without deviating from its spirit and scope as claimed.

What is claimed is:

1. A fixation plate, comprising:

a substantially rigid plate having a longitudinal axis and defining first and second sets of threaded peg holes adapted to individually receive fixation pegs therethrough, said second set of peg holes defining axes that extend between and non-parallel to axes of said first set of peg holes, wherein said first set is arranged substantially along a first line, said second set is arranged substantially along a second line, and said first and second lines are longitudinally offset along said longitudinal axis relative to each other.

2. A fixation plate according to claim 1, wherein:

said rigid plate includes a proximal elongate body portion and a distal head portion at one end of the body portion, and said first and second sets of peg holes are provided in said head portion.

3. A fixation plate according to claim 2, wherein:
said second set of peg holes is offset distally relative to said first set of peg holes.

4. A fixation plate according to claim 3, wherein:
said first set of peg holes defines axes which project distally of said second set of peg holes.

5. A fixation plate according to claim 2, wherein:
said body portion includes at least one screw hole.

6. A fixation plate according to claim 2, wherein:
said head portion is angled relative to the body portion.

7. A fixation plate according to claim 1, wherein:
in said first set of peg holes, at least two of said peg holes define axes which are oblique relative to each other.

8. A fixation plate according to claim 7, wherein:
in said first set of peg holes, at least two of said peg holes define axes which are oblique in two dimensions relative to each other.

9. A fixation plate according to claim 8, wherein:
in said first set of peg holes, each of said holes defines an axis which is oblique in two dimensions relative to the axes of the other peg holes.

10. A fixation plate according to claim 7, wherein
said second set of peg holes define axes parallel to each other.

11. A fixation plate according to claim 1, wherein:
said plate is a substantially T-shaped plate sized for fixation of volar wrist fractures.

12. A fixation plate according to claim 1, wherein:
said first and second sets each include at least three peg holes.

13. A fixation plate according to claim 12, wherein:
said peg holes of said first set are each substantially linearly arranged and said peg holes of said second set are each substantially linearly arranged.

14. A fixation plate, comprising:
a substantially rigid plate having a proximal elongate body portion and a distal head portion at one end of the body portion, said head portion being angled upward relative to said body portion and said head portion defining first and second longitudinally displaced sets of threaded peg holes adapted to individually receive fixation pegs therethrough, wherein said first set is arranged substantially along a first line, said second set is arranged substantially along a second line, and said second line is distally offset on said head portion relative to said first line, and said first set of peg holes laterally overlaps said second set of peg holes.

15. A fixation plate according to claim 14, wherein:
said head portion includes a distal buttress portion having an upper surface which is substantially parallel to said body portion, and said second set of peg holes are in said buttress portion.

16. A fixation plate according to claim 15, wherein:
said second set of peg holes define axes which are substantially perpendicular to said body portion.

17. A fixation plate according to claim 14, wherein:
in said first set of peg holes, at least two of said peg holes define axes which are oblique relative to each other.

18. A fixation plate according to claim 17, wherein:
in said first set of peg holes, at least two of said peg holes define axes which are oblique in two dimensions relative to each other.

19. A fixation plate according to claim 18, wherein:
in said first set of peg holes, each of said peg holes defines an axis which is oblique in two dimensions relative to the axes of the other peg holes.

20. A fixation plate according to claim 14, wherein
said second set of peg holes define axes parallel with each other.

21. A fixation plate according to claim 14, wherein:
said first and second sets each include at least three peg holes.

22. A fixation plate according to claim 21, wherein:
said peg holes of said first set are each substantially linearly arranged and said peg holes of said second set are each substantially linearly arranged.

23. A fixation plate comprising:
a substantially rigid plate including a proximal elongate body portion and a distal head portion at one end of the body portion angled relative to said body portion, said head portion defining first and second sets of threaded peg holes adapted to individually receive fixation pegs therethrough,
wherein said first set of peg holes is arranged substantially along a first line and said head portion includes a distal buttress portion distal of said first line, and said second set of peg holes are in said buttress portion and define axes that extend between and non-parallel to axes of said first set of peg holes.

24. A fixation plate according to claim 23, wherein:
said second set of peg holes define axes which are substantially perpendicular to a longitudinal axis through said body portion.

25. A fixation plate according to claim 23, wherein:
said buttress tapers in thickness in a distal direction.

26. A fixation plate according to claim 23, wherein:
said first and second sets each include at least three peg holes.

27. A fixation plate according to claim 26, wherein:
said peg holes of said first set are each substantially linearly arranged and said peg holes of said second set are each substantially linearly arranged.

28. A fixation plate comprising:
a substantially rigid plate having a proximal elongate body portion and a distal head portion at one end of the body portion, said head portion being angled upward relative to said body portion and said head portion defining first and second longitudinally displaced sets of threaded peg holes adapted to individually receive fixation pegs therethrough, wherein said first set of peg holes is arranged substantially along a first line, said second set of peg holes is arranged substantially along a second line, and said second line is distally offset on said head portion relative to said first line,
wherein said first set of peg holes define axes which project distally of said second set of peg holes.

29. A fracture fixation system, comprising:
a) a substantially rigid plate;
b) a first set of elongate projections coupled to said plate in a substantial linear arrangement on a first line; and
c) a second set of elongate projections coupled to said plate in a substantial linear arrangement on a second line,
wherein said first and second lines are not co-linear, and said second set of projections defines axes that extend between and non-parallel to axes of said first set of projections.

30. A fracture fixation system according to claim 29, wherein
said plate includes a first set of threaded peg holes, and said first set of projections are fixed-angle pegs threaded into said first set of threaded peg holes.

31. A fracture fixation system according to claim 30, wherein
said plate includes a second set of threaded peg holes, and said second set of projections are fixed-angle pegs threaded into said second set of threaded peg holes.

32. A fracture fixation system according to claim 29, wherein:
said plate includes a proximal elongate body portion and a distal head portion at one end of the body portion, and said first and second sets of projections are provided at said head portion.

33. A fracture fixation system according to claim 32, wherein:
said head portion is angled relative to the body portion.

34. A fracture fixation system according to claim 32, wherein:
said head portion includes a distal buttress portion having an upper surface and a lower surface, said upper surface being substantially parallel to said body portion, and said second set of projections extending from said lower surface.

35. A fracture fixation system according to claim 34, wherein:
said second set of projections are substantially perpendicular to said body portion.

36. A fracture fixation system according to claim 29, wherein:
at least two of said projections of said first set of projections are oblique relative to each other.

37. A fracture fixation system according to claim 36, wherein:
at least two of said projections of said first set of projections are oblique in two dimensions relative to each other.

38. A fracture fixation system according to claim 37, wherein:
each of said projections of said first set of projections is oblique relative to the others of said projections.

39. A fracture fixation system according to claim 36, wherein
said projections of said second set of projections are parallel to each other.

40. A fracture fixation system according to claim 29, wherein:
said second set of projections extends from a location distal relative from a location from which said first set of projections extends.

41. A fracture fixation system according to claim 40, wherein:
said first set of projections projects distally of said second set of projections.

42. A fracture fixation system according to claim 29, wherein:
said plate is a substantially T-shaped plate sized for fixation of volar wrist fractures.

43. A fracture fixation system according to claim 29, wherein:
said first and second sets each include at least three projections.

44. A fracture fixation system according to claim 29, wherein:
said projections of said first set extend from substantially linearly arranged locations, and said projections of said second set extend from substantially linearly arranged locations.

45. A fracture fixation system, comprising:
a) a substantially rigid plate having a proximal elongate body portion and a distal head portion including a distal bone contacting surface angled upward relative to said body portion, said plate sized and shaped for placement on a volar side of a distal radius bone;
b) a first set of at least three elongate projections coupled to said head portion and substantially extending from along a first line along said head portion and oriented such that when said plate is placed on the volar side of the distal radius bone said first set of projections enter into the distal radius from the volar side; and
c) a second set of at least two substantially linearly arranged elongate projections coupled to said head portion, said second set of projections extending from a location distal of said first line and oriented such that when said plate is placed on the volar side of the distal radius bone said second set of projections also enter into the distal radius from the volar side,
wherein axes through said first set of projections project distally of axes through said second set of projections.

46. A fracture fixation system according to claim 45, wherein
said plate includes a first set of threaded peg holes, and said first set of projections are fixed-angle pegs threaded into said first set of threaded peg holes.

47. A fracture fixation system according to claim 45, wherein
said plate includes a second set of threaded peg holes, and said second set of projections are fixed-angle pegs threaded into said second set of threaded peg holes.

48. A fracture fixation system according to claim 45, wherein:
said first and second sets of projections are coupled to said plate by at least one of a threaded coupling thereto and a unitary construction with said plate.

49. A fracture fixation system according to claim 45, wherein:
said first and second sets each include at least three projections.

50. A fracture fixation system according to claim 49, wherein:
said projections of said first set extend from substantially linearly arranged locations, and said projections of said second set extend from substantially linearly arranged locations.

51. A fracture fixation system according to claim 45, wherein
said plate includes a first set of holes, and said first set of projections are pegs threaded into said first set of holes, and said plate includes a second set of holes, and said second set of projections are pegs threaded into said second set of holes.

52. A fracture fixation system, comprising:
a) a substantially rigid plate having a proximal elongate body portion and a distal head portion at one end of said body portion;
b) a first set of at least three substantially linearly arranged elongate projections coupled to said head portion; and
c) a second set of at least two substantially linearly arranged elongate projections coupled to said head portion, said second set of projections extending from a location distal from which said first set of projections extends, wherein said first and second sets of projections are laterally overlapping.

53. A fracture fixation system according to claim 52, wherein:
said first and second sets each include at least three projections.

54. A fracture fixation system according to claim 53, wherein:
said projections of said first set extend from substantially linearly arranged locations, and said projections of said second set extend from substantially linearly arranged locations.

55. A fracture fixation system according to claim 52, wherein:
said first and second sets of projections are fixed angle projections.

56. A fracture fixation system, comprising:
a) a substantially rigid plate including a proximal elongate body portion and a distal head portion at one end of the body portion;
b) a first set of elongate projections coupled to said head portion of said plate, said plate defining a tapered buttress portion distal of where said first set of elongate projections are coupled to said head portion; and
c) a second set of elongate projections coupled to said tapered buttress portion,
wherein said second set of projections defines axes that extend between and non-parallel to axes of said first set of projections.

57. A fracture fixation system according to claim 56, wherein:
said first set of projections is a substantially linear arrangement of projections, and said second set is substantially linear arrangement of projections.

58. A fracture fixation system, comprising:
a) a substantially rigid plate having a proximal elongate body portion and a distal head portion angled upward relative to said body portion;
b) a first set of at least three substantially linearly arranged elongate projections coupled to said head portion; and
c) a second set of at least two substantially linearly arranged elongate projections coupled to said head portion, said second set of projections extending from a location distal from which said first set of projections extends,
wherein axes through said first set of projections project distally of axes through said second set of projections.

* * * * *